United States Patent
Kurihara et al.

(10) Patent No.: US 9,624,516 B2
(45) Date of Patent: *Apr. 18, 2017

(54) MANUFACTURING METHOD FOR SUGAR SOLUTION AND DEVICE FOR SAME

(75) Inventors: Hiroyuki Kurihara, Kamakura (JP); Atsushi Minamino, Kamakura (JP); Yuki Yamamoto, Kamakura (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 130 days.

This patent is subject to a terminal disclaimer.

(21) Appl. No.: 13/634,961

(22) PCT Filed: Mar. 14, 2011

(86) PCT No.: PCT/JP2011/055903
§ 371 (c)(1),
(2), (4) Date: Nov. 8, 2012

(87) PCT Pub. No.: WO2011/115040
PCT Pub. Date: Sep. 22, 2011

(65) Prior Publication Data
US 2013/0203117 A1     Aug. 8, 2013

(30) Foreign Application Priority Data

Mar. 15, 2010 (JP) ................. 2010-057402

(51) Int. Cl.
*C12M 1/00* (2006.01)
*C12P 19/00* (2006.01)
(Continued)

(52) U.S. Cl.
CPC ............. *C12P 19/00* (2013.01); *C12M 21/18* (2013.01); *C12M 29/04* (2013.01); *C12M 33/14* (2013.01); *C12P 19/14* (2013.01); *C13K 1/02* (2013.01)

(58) Field of Classification Search
CPC ....... C12P 19/02; C12P 19/14; C12P 2201/00; C12P 2203/00; C12R 1/885;
(Continued)

(56) References Cited

U.S. PATENT DOCUMENTS 3,642,580 A * 2/1972 Ghose .......................... 435/105
3,764,475 A * 10/1973 Mandels et al. ............... 435/105
(Continued)

FOREIGN PATENT DOCUMENTS

JP   55-144885 A   11/1980
JP   63-087994 A    4/1988
(Continued)

OTHER PUBLICATIONS

Microsoft translation of JP 2006-087319 with original document attached, translated from WIPO website Nov. 29, 2013.*
(Continued)

*Primary Examiner* — Ralph Gitomer
*Assistant Examiner* — Trent Clarke
(74) *Attorney, Agent, or Firm* — DLA Piper LLP (US)

(57) ABSTRACT

A method produces a sugar liquid by repeating a sugar liquid production process including (1) to (3): (1) adding a filamentous fungus-derived cellulase to cellulose to perform primary hydrolysis; (2) adding a fresh filamentous fungus-derived cellulase to the hydrolysate in Step (1) to perform secondary hydrolysis; and (3) subjecting the hydrolysate in Step (2) to solid-liquid separation to obtain a sugar liquid, from which a recovered enzyme is obtained; wherein the recovered enzyme obtained in Step (3) is used for Step (1) of the next and later sugar liquid production processes.

11 Claims, 9 Drawing Sheets

(51) Int. Cl.
 *C12P 19/14* (2006.01)
 *C13K 1/02* (2006.01)
 *C12M 1/40* (2006.01)
 *C12M 1/26* (2006.01)

(58) Field of Classification Search
 CPC .... C12Y 302/01004; C12Y 302/01008; C12Y 302/01032; C12Y 302/01037; C12Y 302/01072; C12Y 302/01131; C12Y 302/01156
 See application file for complete search history.

(56) References Cited

U.S. PATENT DOCUMENTS

| | | | | |
|---|---|---|---|---|
| 4,220,721 | A | * | 9/1980 | Emert et al. ............ 435/165 |
| 4,461,648 | A | * | 7/1984 | Foody ..................... 127/37 |
| 4,713,334 | A | * | 12/1987 | Fujishima ............ C12P 19/14 435/162 |

FOREIGN PATENT DOCUMENTS

| | | | |
|---|---|---|---|
| JP | 11-506934 | A | 6/1999 |
| JP | 3041380 | B2 | 5/2000 |
| JP | 2001-095597 | A | 4/2001 |
| JP | 2003-212888 | A | 7/2003 |
| JP | 2005-229821 | A | 9/2005 |
| JP | 2006-087319 | A | 4/2006 |
| JP | 2008-161125 | A | 7/2008 |
| JP | 2008-206484 | A | 9/2008 |
| JP | 2008-535664 | A | 9/2008 |
| JP | 2010-098951 | A | 5/2010 |

OTHER PUBLICATIONS

Tony Collins, Charles Gerday, and Georges Feller, Xylanases, xylanase families and extremophilic xylanases, 2005, FEMS Microbiology Reviews, vol. 29, pp. 3-23.*
Sugiura et al., JP 2006-087319, Espacenet translation generated Oct. 30, 2014.*
Bernie Steele, Srini Raj, John Nghiem, and Mark Stowers, Enzyme Recovery and Recycling Following Hydrolysis of Ammonia Fiber Explosion-Treated Corn Stover, 2005, Applied Biochemistry and Biotechnology, vol. 121-124,, pp. 901-910.*
Geoffrey Moxley, Zhiguang Zhu, and Y.-H. Percival Zhang, Efficient Sugar Release by the Cellulose Solvent-Based Lignocellulose Fractionation Technology and Enzymatic Cellulose Hydrolysis, 2008, J. Agric. Food Chem., vol. 56, pp. 7885-7890.*
Jing Yang, Xiaoping Zhang, Qiang Yong, Shiyuan Yu, Three-stage hydrolysis to enhance enzymatic saccharification of steam-exploded corn stover, 2010, Bioresource Technology, vol. 101, pp. 4930-4935, published online Oct. 25, 2009.*
Mary Mandels, John E. Medeiros, Raymond E. Andreotti, and Frank H. Bissett, Enzymatic Hydrolysis of Cellulose: Evaluation of Cellulase Culture Filtrates under Use Conditions, 1981, Biotechnology and Bioengineering, vol. 23, pp. 2009-2026.*
A. Aden et al., "Lignocellulosic Biomass to Ethanol Process Design and Economics Utilizing Co-Current Dilute Acid Prehydrolysis and Enzymatic Hydrolysis for Corn Stover," NREL Technical Report, 2002 (Abstract).

* cited by examiner

MANUFACTURING METHOD FOR SUGAR SOLUTION AND DEVICE FOR SAME

RELATED APPLICATIONS

This is a §371 of International Application No. PCT/JP2011/055903, with an international filing date of Mar. 14, 2011 (WO 2011/115040 A1, published Sep. 22, 2011), which is based on Japanese Patent Application No. 2010-057402, filed Mar. 15, 2010, the subject matter of which is incorporated by reference.

TECHNICAL FIELD

This disclosure relates to a method for producing a sugar liquid from cellulose, and an apparatus for the method.

BACKGROUND

Processes of fermentation production of chemical products using sugars as raw materials have been used for producing various industrial materials. At present, as the sugars to be used as fermentation feedstocks, those derived from food materials such as sugar cane, starch and sugar beet are industrially used. However, in view of the fact that rise in the prices of food materials due to future increase in the world population is expected, or in an ethical view of the fact that sugars for industrial materials may compete with sugars for food, a process for efficiently producing a sugar liquid from a renewable nonfood resource, that is, a cellulose-containing biomass, or a process for using an obtained sugar liquid as a fermentation feedstock to efficiently convert the sugar liquid to an industrial material needs to be constructed in the future.

Examples of disclosed methods for producing a sugar liquid from a cellulose-containing biomass include methods for producing sugar liquids by acid hydrolysis of cellulose and hemicellulose using concentrated sulfuric acid (Japanese Translated PCT Patent Application Laid-open No. 11-506934 and JP 2005-229821 A) and a method wherein a cellulose-containing biomass is subjected to hydrolysis treatment using dilute sulfuric acid and then enzymatically treated with cellulase or the like to produce a sugar liquid (A. Aden et al., "Lignocellulosic Biomass to Ethanol Process Design and Economic Utilizing Co-Current Dilute Acid Prehydrolysis and Enzymatic Hydrolysis for Corn Stover," NREL Technical Report (2002)). Further, examples of disclosed methods using no acid include a method wherein a cellulose-containing biomass is hydrolyzed using subcritical water at about 250° C. to 500° C. to produce a sugar liquid (JP 2003-212888 A), a method wherein a cellulose-containing biomass is subjected to subcritical water treatment and then enzymatically treated to produce a sugar liquid (JP 2001-95597 A), and a method wherein a cellulose-containing biomass is subjected to hydrolysis treatment with presurized hot water at 240° C. to 280° C. and then enzymatically treated to produce a sugar liquid (JP 3041380 B).

In recent years, methods of hydrolysis of a biomass which use less energy and cause less environmental load, but produce sugar at high yields have been extensively studied. However, such methods using enzymes have a drawback in that the costs of enzymes are high.

To solve these technical problems, methods of recovering and reusing the enzymes used in the hydrolysis have been proposed. Examples of such methods include a method wherein continuous solid-liquid separation is carried out with a spin filter and the obtained sugar liquid is filtered through an ultrafiltration membrane to recover the enzymes (JP 2006-87319 A), a method wherein a surfactant is fed at the stage of enzymatic saccharification to suppress enzyme adsorption and thereby enhance the recovery efficiency (JP 63-87994 A), a method wherein the residue produced by enzymatic saccharification is subjected to electric treatment to recover the enzyme component (JP 2008-206484 A) and a method wherein the residue produced by enzymatic saccharification is fed again to another batch of biomass and the enzymes is thereby reused (JP 55-144885 A).

Methods of enzymatic hydrolysis of cellulose have been developed as described above, but the effects of these methods have been insufficient in view of reduction in the amount of the enzyme used. Therefore, it could be helpful to provide a process wherein the effect of reducing the amount of the enzyme used is higher than those in the conventional methods.

SUMMARY

We thus provide:

[1] A method for producing a sugar liquid by repeating a sugar liquid production process comprising Steps (1) to (3) below:
   (1) adding a filamentous fungus-derived cellulase to cellulose to perform primary hydrolysis;
   (2) adding a fresh filamentous fungus-derived cellulase to the hydrolysate in Step (1) to perform secondary hydrolysis; and
   (3) subjecting the hydrolysate in Step (2) to solid-liquid separation to obtain a sugar liquid, from which a recovered enzyme is obtained;
wherein the recovered enzyme obtained in Step (3) is used for Step (1) of next and later sugar liquid production processes.

[2] The method for producing a sugar liquid according to [1], wherein, as the filamentous fungus-derived cellulase in the Step (1) of the sugar liquid production process, an enzyme component recovered from a cellulose hydrolysate produced by a filamentous fungus-derived cellulase is used.

[3] The method for producing a sugar liquid according to [1] or [2], wherein the filamentous fungus-derived cellulase in the Step (1) or (2) comprises a component derived from a culture liquid of a microorganism belonging to the genus *Trichoderma*.

[4] The method for producing a sugar liquid according to any of [1] to [3], wherein the recovered enzyme comprises xylanase and/or xylosidase.

[5] The method for producing a sugar liquid according to any of [1] to [4], wherein the recovered enzyme comprises a water-insoluble filamentous fungus-derived cellulase.

[6] The method for producing a sugar liquid according to any of [1] to [5], wherein the cellulose is a processed product obtained by subjecting a cellulose-containing biomass to alkaline treatment, hydrothermal treatment or dilute sulfuric acid treatment.

[7] The method for producing a sugar liquid according to any of [1] to [6], wherein the amounts of enzyme added in the primary hydrolysis and the secondary hydrolysis satisfy the following relation: the amount of the recovered enzyme added in Step (1)>the amount of the fresh enzyme added in Step (2).

[8] The method for producing a sugar liquid according to any of [1] to [7], wherein the recovery of the filamentous fungus-derived cellulase in the Step (3) is carried out by filtering the sugar liquid through an ultrafiltration membrane and recovering the cellulase from the feed side.

[9] An apparatus for a method for producing a sugar liquid, the method comprising the step of hydrolyzing cellulose, the apparatus comprising, as constituents: a hydrolysis tank to which a recovered enzyme feed pipe and a fresh enzyme feed pipe are connected; device for solid-liquid separation of a hydrolysate; sugar liquid-retaining tank having a water supply pipe for washing an ultrafiltration membrane and/or for removing recovered enzyme retained in a circulation pipe; and ultrafiltration membrane device for separation of enzyme and a sugar liquid.

[10] An apparatus for a method for producing a sugar liquid, the method comprising the step of hydrolyzing cellulose, the apparatus comprising, as constituents: a cellulose/recovered enzyme-mixing device for mixing recovered enzyme and cellulose to perform primary hydrolysis; hydrolysis tank to which a cellulose/recovered enzyme mixture supply pipe and a fresh enzyme feed pipe are connected; device for solid-liquid separation of a hydrolysate; sugar liquid-retaining tank having a water supply pipe for washing an ultrafiltration membrane and/or for removing recovered enzyme retained in a circulation pipe; and ultrafiltration membrane device for separation of enzyme and a sugar liquid.

[11] An apparatus comprising, as a constituent(s), in addition to the apparatus constituents recited in [9] or [10], a reverse osmosis membrane and/or nanofiltration membrane device(s) for concentrating the sugar liquid.

In a method of hydrolysis wherein cellulase is recovered and reused, the amount of enzyme used for the hydrolysis can be largely reduced and the efficiency of sugar production from a cellulose-containing biomass can be largely increased by adding, before addition of fresh enzyme, recovered enzyme to perform primary hydrolysis and then further adding fresh enzyme to perform secondary hydrolysis.

DESCRIPTION OF SYMBOLS

Figure 1:
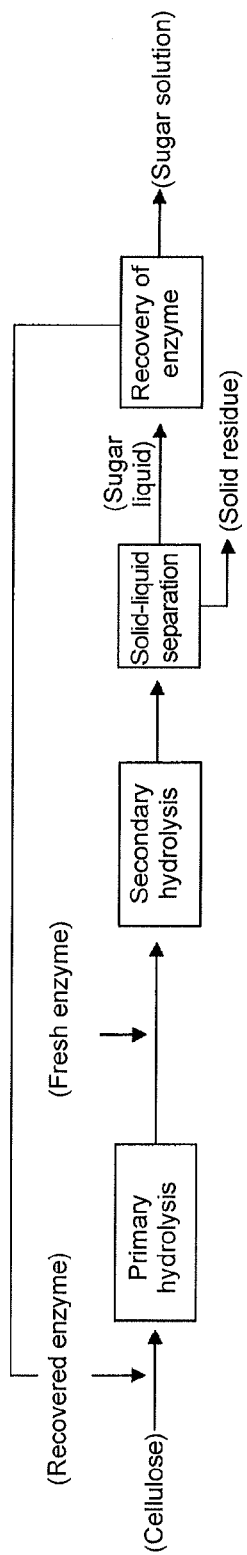
FIG. 1 is a schematic diagram showing the procedure of the method of hydrolysis.

1 Hydrolysis tank
2 Thermostat
3 Stirring blade
4 Recovered enzyme feed pipe
5 Recovered enzyme-retaining tank
6 Fresh enzyme feed pipe
7 Cellulose inlet
8 Fresh enzyme-retaining tank
9 Press filtration device
10 Compressor
11 Water supply pipe
12 Sugar liquid-retaining tank
13 Circulation pump
14 Ultrafiltration membrane device
15 Circulation pipe
16 Recovered enzyme pipe
17 Cellulose/recovered enzyme mixture supply pipe
18 Cellulose/recovered enzyme-mixing device
19 Solid-liquid separation device
20 Solids discharge pipe
21 Three-way valve
22 Microfiltration membrane device
23 Solid-liquid separation filtrate tank
24 Pump
25 Microfiltration membrane
26 Compressed-air supply device
27 Reverse-washing pump
28 Sugar liquid concentrating tank
29 High-pressure pump
30 Reverse osmosis membrane and/or nanofiltration membrane device
31 Three-way valve

DETAILED DESCRIPTION

Large amounts of celluloses are contained in herbaceous biomasses such as bagasse, switchgrass, napier grass, *Erianthus*, corn stover, rice straw and wheat straw; and woody biomasses such as trees and waste building materials. These cellulose-containing biomasses can be preferably used as raw materials.

Cellulose-containing biomass contains, in addition to cellulose and hemicellulose (hereinafter referred to as "cellulose" as a general term for cellulose and hemicellulose), lignin and the like which are aromatic macromolecules. Therefore, in cases where cellulose derived from a biomass is used as a raw material for a sugar liquid in the method for producing a sugar liquid, the efficiency of enzymatic hydrolysis can be enhanced by pretreatment. Examples of the method of pretreatment of a cellulose-containing biomass include acid treatment, sulfuric acid treatment, dilute sulfuric acid treatment, alkaline treatment, caustic soda treatment, hydrothermal treatment, subcritical water treatment, pulverization treatment and steaming treatment. The method of pretreatment is preferably alkaline treatment, hydrothermal treatment or dilute sulfuric acid treatment.

Examples of the alkaline treatment include methods using an alkali such as sodium hydroxide, calcium hydroxide or ammonia, and ammonia can be especially preferably used. Such ammonia treatment can be performed by the methods described in JP 2008-161125 A and JP 2008-535664 A. For example, ammonia is added to the biomass at a concentration within the range of 0.1 to 15% by weight, and the treatment is carried out at 4 to 200° C., preferably 90 to 150° C. The ammonia to be added may be in the state of either liquid or gas. Further, the form of the ammonia to be added may be either pure ammonia or aqueous ammonia. The number of times of the treatment is not restricted, and one or more times of the treatment may be carried out. In particular, in cases where the treatment is carried out two or more times, the conditions for the first treatment may be different from those for the second and later treatments. The treated product obtained by the ammonia treatment needs to be subjected to neutralization of ammonia or removal of ammonia to further carry out enzymatic hydrolysis reaction. The neutralization of ammonia may be carried out either after removal of the solids from the hydrolysate by solid-liquid separation or in the state in which the solids are contained. The acid reagent to be used for the neutralization is not restricted. The ammonia can be removed by maintaining the ammonia-treated product under reduced pressure to allow evaporation of the ammonia into the state of gas. The removed ammonia may be recovered and reused.

In the case of hydrothermal treatment, water is added such that the concentration of the cellulose-containing biomass is 0.1 to 50% by weight, and the resulting mixture is treated at a temperature of 100 to 400° C. for 1 second to 60 minutes. By treatment under such temperature conditions, hydrolysis of cellulose occurs. The number of times of the treatment is not restricted, and one or more times of the treatment may be carried out. In particular, in cases where the treatment is carried out two or more times, the conditions for the first treatment may be different from those for the second and later treatments.

In the case of dilute sulfuric acid treatment, the concentration of sulfuric acid is preferably 0.1 to 15% by weight, more preferably 0.5 to 5% by weight. The reaction temperature may be set within the range of 100 to 300° C., and is preferably set within the range of 120 to 250° C. The reaction time may be set within the range of 1 second to 60 minutes. The number of times of the treatment is not restricted, and one or more times of the treatment may be carried out. In particular, in cases where the treatment is carried out two or more times, the conditions for the first treatment may be different from those for the second and later treatments. Since the hydrolysate obtained by the dilute sulfuric acid treatment contains acid, neutralization is necessary to further carry out hydrolysis reaction with cellulose or to use the hydrolysate as a fermentation feedstock.

The method is characterized in that the cellulose is hydrolyzed with a filamentous fungus-derived cellulase. The hydrolysis of cellulose means that cellulose is made into low molecular weight fragments by the action of cellulase to produce monosaccharides and/or oligosaccharides. The reaction conditions for the hydrolysis are not restricted as long as the reaction is performed under conditions preferred by the cellulose and, in general, the reaction temperature is preferably within the range of 15° C. to 100° C., more preferably 40° C. to 60° C., still more preferably 50° C. The pH for the hydrolysis is preferably within the range of 3 to 9, more preferably 4 to 5.5, still more preferably 5. The pH can be adjusted by adding an acid or alkali such that a desired pH is achieved. Further, a buffer may be added as appropriate. In the hydrolysis, it is preferred to stir the mixture to promote contacting of cellulose with the enzyme and to make the sugar concentration in the hydrolysate uniform. It is preferred to add water such that the solids concentration of the cellulose is within the range of 1 to 25% by weight, and the solids concentration is more preferably within the range of 8 to 20% by weight.

Examples of the filamentous fungus-derived cellulase include those derived from *Trichoderma, Aspergillus, Cellulomonas, Clostridium, Streptomyces, Humicola, Acremonium, Irpex, Mucor, Talaromyces, Phanerochaete*, white-rot fungi and brown-rot fungi. Among such filamentous fungus-derived cellulases, *Trichoderma*-derived cellulase, which has high cellulose-degrading activity, is preferably used.

The *Trichoderma*-derived cellulase is an enzyme composition comprising cellulase derived from a microorganism belonging to the genus *Trichoderma* as a major component. The microorganism belonging to the genus *Trichoderma* is not restricted, and *Trichoderma reesei* is preferred. Specific examples of the *Trichoderma reesei* include *Trichoderma reesei* QM9414, *Trichoderma reesei* QM9123, *Trichoderma reesei* Rut C-30, *Trichoderma reesei* ATCC68589, *Trichoderma reesei* PC3-7, *Trichoderma reesei* CL-847, *Trichoderma reesei* MCG77, *Trichoderma reesei* MCG80 and *Trichoderma viride* QM9123 (*Trichoderma viride* 9123). The cellulase may also be derived from a mutant strain originated from the microorganism belonging to the genus *Trichoderma*, which mutant strain was prepared by mutagenesis using a mutagen, UV irradiation or the like to enhance the cellulase productivity.

The filamentous fungus-derived cellulase is an enzyme composition comprising a plurality of enzyme components such as cellobiohydrolase, endoglucanase, exoglucanase, β-glucosidase, xylanase and xylosidase, which enzyme composition has an activity to hydrolyze and saccharify cellulose. In cases where the filamentous fungus-derived cellulase is used for degradation of cellulose, a concerted effect or complementary effect by the plurality of enzyme components enables efficient hydrolysis of cellulose.

Cellobiohydrolase is a general term for cellulases that hydrolyze cellulose from the terminal portions. The group of enzymes belonging to cellobiohydrolase are described as EC number: EC 3.2.1.91.

Endoglucanase is a general term for cellulases that hydrolyze cellulose molecular chains from their central portions. The group of enzymes belonging to endoglucanase are described as EC numbers: EC 3.2.1.4, EC 3.2.1.6, EC 3.2.1.39 and EC 3.2.1.73.

Exoglucanase is a general term for cellulases that hydrolyze cellulose molecular chains from their termini. The group of enzymes belonging to exoglucanase are described as EC numbers: EC 3.2.1.74 and EC 3.2.1.58.

β-glucosidase is a general term for cellulases that acts on cellooligosaccharides or cellobiose. The group of enzymes belonging to β-glucosidase are described as EC number: EC 3.2.1.21.

Xylanase is a general term for cellulases that acts on hemicellulose or especially xylan. The group of enzymes belonging to xylanase are described as EC number: EC 3.2.1.8.

Xylosidase is a general term for cellulases that acts on xylooligosaccharides. The group of enzymes belonging to xylosidase are described as EC number: EC 3.2.1.37.

As the *Trichoderma*-derived cellulase, one comprising a component(s) derived from a culture liquid of a microorganism belonging to the genus *Trichoderma* is preferably used. Examples of the component(s) derived from a *Trichoderma*-derived culture liquid include all the components other than cellulase contained in a culture liquid obtained by culturing a microorganism belonging to the genus *Trichoderma* in a medium prepared such that the microorganism produces cellulase. That is, examples of the component(s) include the enzyme components other than cellulase, cells of the microorganism belonging to the genus *Trichoderma*, and medium components used for the culture. Specific examples of the medium components used for the culture include monosaccharides such as glucose and xylose; cellulase production inducers such as corn steep liquor, yeast extract, and cellulose; minerals; and vitamin components. Cells of a microorganism belonging to the genus *Trichoderma* may be contained as a component derived from a culture liquid of a microorganism belonging to the genus *Trichoderma*. This is because inclusion of cells of a microorganism belonging to the genus *Trichoderma* as a component of the *Trichoderma*-derived cellulase can enhance the activity of the recovered enzyme.

The weight ratios of enzyme components in the *Trichoderma*-derived cellulase are not restricted and, for example, a culture liquid derived from *Trichoderma reesei* contains 50 to 95% by weight cellobiohydrolase, and also contains as other components endoglucanase, β-glucosidase, exo-1,4-β-D-glucosamidase, xylanase, xylosidase, endo-1, 4-mannosidase, 1,2-α-mannosidase, α-glucuronidase, chitosanase, chitinase, 1,4-α-glucosidase, α-galactosidase, β-galactosidase, arabinofuranosidase, xylan esterase, swollenin, hydrophobin and/or the like. Microorganisms belonging to *Trichoderma* produce strong cellulase components into the culture liquid, while the β-glucosidase activity in the culture liquid is low since β-glucosidase is retained in the cells or on the cell surfaces. Therefore, in addition to the inherent *Trichoderma*-derived cellulase components, β-glucosidase from a different species or from the same species may be added. As the β-glucosidase from a different species, β-glucosidase derived from *Aspergillus* may be preferably used. Examples of the β-glucosidase derived from *Aspergillus* include Novozyme 188, which is commercially available from Novozyme. The method of addition of β-glucosidase from a different species or from the same species may be a method wherein a gene is introduced to a microorganism belonging to *Trichoderma* to perform genetic recombination of the microorganism such that β-glucosidase is produced into the culture liquid, and the micro-organism belonging to *Trichoderma* is then cultured, followed by isolating the culture liquid.

Hydrolysis of cellulose with the filamentous fungus-derived cellulase is carried out in two separate steps, that is, primary hydrolysis and secondary hydrolysis. The steps are described below in order.

The primary hydrolysis means that a filamentous fungus-derived cellulase is added to cellulose that has not been subjected to enzyme treatment, to perform hydrolysis. The enzyme used for the primary hydrolysis may be either the later-mentioned fresh enzyme or recovered enzyme, and recovered enzyme is preferably used since use of the recovered enzyme can increase the efficiency of sugar production. The mechanisms by which the efficiency of sugar production is increased by using recovered enzyme in the primary hydrolysis are as follows. In the recovered enzyme, enzyme components whose structures were partially denatured due to the heat during the hydrolysis are contained, and such enzyme components exhibit especially strong adsorption to adsorption sites existing on the surfaces of cellulose. As a result, the enzyme components are non-specifically adsorbed to the adsorptive surface portions in the cellulose, such as lignin. Therefore, nonspecific adsorption of the fresh enzyme component that is fed later can be suppressed. In general, the specific activity (enzymatic activity per protein weight) of degradation by cellulase is higher in the recovered enzyme than in the fresh enzyme. That is, as a result of suppression of nonspecific adsorption of the fresh enzyme component, which has higher specific activity, the sugar productivity and the efficiency of recovery of the enzyme can be increased. Another reason is that, as the number of times of recovery of the recovered enzyme of the present invention increases, higher xylan-degrading activity can be obtained. The xylan-degrading activity contained in the recovered enzyme can be measured using as a substrate to be degraded a reagent xylan such as birch wood xylan. Examples of filamentous fungus-derived cellulase components involved in the xylan-degrading activity include xylanase and xylosidase. Examples of the genes for xylanase include xyn1(GH11), xyn2(GH11), xyn3(GH10), xyn4 (GH5), xyn5b(GH5) and xyn11(GH11). Examples of the genes for xylosidase include bxl1/bxl3a(GH3), bxl3b(GH3) and bxl3c(GH3). Each of the above genes encodes xylanase or xylosidase, and is contained as a filamentous fungus-derived cellulase component. Examples of xylan-degrading enzymes whose activities in the recovered enzyme can be increased include xylanase 3 (molecular weight, 38 kDa; xyn3), endo-β-1,4-xylanase (molecular weight, 25 kDa; xyn1) and β-xylosidase (molecular weight, 88 kDa; bxl1/ bxl3a). By adding the recovered enzyme, whose xylan-degrading activity was enhanced as described above, for the primary hydrolysis, the xylan components surrounding cellulose are preferentially hydrolyzed, and the sugar productivity in the primary and secondary hydrolysis can therefore be enhanced.

The reaction time in the primary hydrolysis is preferably within the range of 15 minutes to 6 hours. In cases where the reaction time is less than 15 minutes, the degree of enhancement of the efficiency of sugar production may be low, while in cases where the reaction time is not less than 6 hours, the efficiency of sugar production per unit time may be low. The cellulose concentration, reaction temperature and pH are not restricted, and may be those in the above-described conditions for hydrolysis.

The enzyme for the primary hydrolysis is preferably added at a weight ratio of 1/1000 to 1/50 with respect to the weight of the pretreated cellulose. The weight of the pretreated cellulose can be calculated by measuring the weight of the solid content contained in the pretreated cellulose. The weight of the solids can be calculated by subjecting the pretreated product to solid-liquid separation by centrifugation, membrane separation or the like and washing the resultant with water to separate and remove water-soluble compounds, followed by drying the water-containing solids until the weight reaches a constant value and measuring the weight of the solids. The amount of enzyme added can be calculated by measuring the protein concentration in the solution containing the fresh enzyme and multiplying the protein concentration by the amount of the solution of the fresh enzyme added.

In the primary hydrolysate obtained by the primary hydrolysis, monosaccharide components produced by the hydrolysis are accumulated. The xylan-degrading activity tends to be high especially in cases where recovered enzyme is used for the primary hydrolysis. That is, in the primary hydrolysate obtained by using recovered enzyme in the primary hydrolysis, a large amount of xylose is produced. The primary hydrolysate obtained by the primary hydrolysis may be subjected to the later-mentioned secondary hydrolysis as it is or after performing an operation such as solid-liquid separation to enhance the concentration of undegraded solids. Further, in cases where solid-liquid separation is performed after the primary hydrolysis, the solution component obtained by the separation may be used as a sugar liquid.

The secondary hydrolysis means that fresh enzyme is further added to the hydrolysate obtained by the above-described primary hydrolysis, to perform hydrolysis. The solid-liquid separation operation does not need to be carried out for the primary hydrolysate. Further, as required, water may be added, but the addition of water is not indispensable.

Fresh enzyme is fed and used for the secondary hydrolysis. This is carried out because 1) since a sufficient efficiency of cellulose degradation cannot be obtained with the amount of enzyme fed in the primary hydrolysis (fresh enzyme or recovered enzyme), fresh enzyme needs to be additionally fed to obtain a sufficient efficiency of cellulose degradation; and 2) the sugar production efficiency and the enzyme recovery efficiency can be increased by feeding of fresh enzyme in two separate steps, that is, in the primary hydrolysis and in the secondary hydrolysis. Further, especially in cases where only the primary hydrolysis using recovered enzyme is carried out, the sugar yield in the second and later processes decreases, which is not preferred. Therefore, by feeding fresh enzyme, in addition to the recovered enzyme, for the secondary hydrolysis, the sugar yield can be equivalent to that in the first process or the previous process. That is, in our method for producing a sugar liquid, it is possible to repeat production of sugar at a concentration of not less than a predetermined value.

The addition of fresh enzyme for the secondary hydrolysis may be carried out dividedly a plurality of times (divided feeding). For example, after the primary hydrolysis, a half of the fresh enzyme to be added for the secondary hydrolysis may be fed to carry out hydrolysis for several hours, followed by feeding of the remaining half of the fresh enzyme. Even in cases where fresh enzyme is fed dividedly several times in the secondary hydrolysis, these operations are also included in the secondary hydrolysis.

The reaction time of the secondary hydrolysis is preferably longer than that of the primary hydrolysis. More specifically, the reaction time of the secondary hydrolysis is preferably within the range of 1 to 200 hours, more preferably within the range of 6 to 72 hours, still more preferably within the range of 12 to 24 hours. Although the reaction time should be controlled depending on the amount of enzyme used, reaction temperature, sugar concentration of interest and the like, a reaction time longer than 200 hours may cause heat inactivation of the cellulase, which is not preferred in view of recovery and reuse of the cellulase. On the other hand, in cases where the reaction time is less than 1 hour, the sugar concentration of the obtained hydrolysate may be insufficient.

The enzyme for the secondary hydrolysis is preferably added at a weight ratio of 1/1000 to 1/50 with respect to the weight of the pretreated cellulose. The weight of the pretreated cellulose can be calculated from the weight of the solid content of the pretreated cellulose before the primary hydrolysis.

The amounts of enzyme added in the primary hydrolysis and the secondary hydrolysis preferably satisfy the following relation: the amount of enzyme added for the primary hydrolysis>the amount of enzyme added for the secondary hydrolysis. The amount of addition herein can be calculated by multiplying the protein concentration of the fresh enzyme or recovered enzyme by the amount of the enzyme solution to be fed. In terms of measurement of the protein concentration, the protein concentration of the recovered enzyme and fresh enzyme can be calculated by the above-described known method. The protein concentration herein simply means the protein concentration, irrespective of whether the protein is a cellulase-derived component or another component. When the amount of addition satisfies this relation, a higher sugar production can be achieved, and the efficiency of recovery of the enzyme can also be increased.

The method has the step of subjecting the secondary hydrolysate to solid-liquid separation to obtain a sugar liquid, from which a filamentous fungus-derived cellulase is then recovered; and the step of reusing the recovered filamentous fungus-derived cellulase in the primary hydrolysis. The steps are described below in order.

The solid-liquid separation of the secondary hydrolysate is carried out for the purpose of separating the sugar liquid and the hydrolysis residue obtained by the secondary hydrolysis. The sugar liquid means the sugar solution obtained by the above-described hydrolysis of cellulose. Sugars are generally classified, based on the degree of polymerization of monosaccharides, into monosaccharides such as glucose and xylose; oligosaccharides produced by dehydration condensation of 2 to 9 monosaccharides; and polysaccharides produced by dehydration condensation of not less than 10 monosaccharides. The sugar liquid obtained comprises glucose and xylose as major components and, although in small amounts, oligosaccharides such as cellobiose; and monosaccharides such as arabinose and mannose. More specifically, the method of analysis of monosaccharides, oligosaccharides and polysaccharides dissolved in water may be HPLC, by which the quantification can be carried out based on comparison with a standard sample. The method of solid-liquid separation is not restricted, and examples of the method of solid-liquid separation include centrifugation using a screw decanter or the like, filtration using a filter press or the like, and membrane separation using a microfiltration membrane or the like.

In the secondary hydrolysate, the filamentous fungus-derived cellulase exists in the state where it is dissolved in a sugar liquid or adsorbed to the solid residue as an undegraded material. Such a filamentous fungus-derived cellulase can be recovered by the solid-liquid separation from the sugar liquid side. Preferred examples of the method for recovering the filamentous fungus-derived cellulase from the sugar liquid include a method wherein the sugar liquid is filtered through an ultrafiltration membrane and the cellulase is recovered from the feed side. Examples of the ultrafiltration membrane which may be used include membranes made of materials such as polyether sulfone (PES), polyvinylidene fluoride (PVDF) and regenerated cellulose, but, since regenerated cellulose is degraded by cellulase, an ultrafiltration membrane made of a synthetic polymer material such as PES or PVDF is preferably used. The molecular weight cutoff of the ultrafiltration membrane is not restricted as long as the cellulase to be used can be efficiently recovered, and the ultrafiltration membrane preferably has a molecular weight cutoff within the range of 1000 to 50000. The amount of enzyme recovered varies depending on the amount of the fresh enzyme added for the secondary hydrolysis, and is therefore not restricted.

In the operation of repeating the recovery and reuse, and especially in the process of separation of the recovered enzyme using an ultrafiltration membrane, a water-insoluble filamentous fungus-derived cellulase component may be obtained as a recovered enzyme component in some cases. Such a water-insoluble filamentous fungus-derived cellulase component is an enzyme component produced during the hydrolysis process or during the recovery of enzyme using an ultrafiltration membrane or the like. Such a water-insoluble filamentous fungus-derived cellulase component is preferably used as it is, without being removed by solid-liquid separation, filtration or the like, as a recovered enzyme component. The water-insoluble filamentous fungus-derived cellulase component is constituted mainly of cellobiohydrolase. The water insolubility means that the component exists in the recovered enzyme liquid as precipitates, flocs or microparticles, which can be separated by placing the recovered enzyme in a tube and centrifuging the tube to obtain the water-insoluble filamentous fungus-derived cellulase component as precipitates. The water-insoluble filamentous fungus-derived cellulase component recovered as precipitates can be identified based on its color, which may be white, pale yellow, brown or the like. By separating the water-insoluble filamentous fungus-derived cellulase component and resuspending it in water, a part of the component can be dissolved. However, for complete dissolution of the component, addition of urea or a surfactant (sodium dodecyl sulfate, Tween 80, Triton X or the like) is necessary. By reusing the recovered enzyme containing such a water-insoluble filamentous fungus-derived cellulase component for the primary hydrolysis, still higher sugar productivity can be achieved.

The filamentous fungus-derived cellulase recovered from the secondary hydrolysate (hereinafter referred to as recovered enzyme) is reused for the primary hydrolysis. The advantages of use of the recovered enzyme in the primary hydrolysis are as described above. The number of times of reuse of the recovered enzyme is not restricted.

The amount of enzyme added upon reuse of the enzyme recovered from the secondary hydrolysate for the primary hydrolysis is preferably larger than the amount of fresh enzyme added for the secondary hydrolysis. The amount of addition of enzyme is measured in terms of the protein amount as described above. In general, the cellulase activity of the recovered enzyme (enzyme activity per protein amount) is lower than the cellulase activity of the fresh enzyme, but, in cases where the relation: the amount of addition of recovered enzyme to be reused for the primary hydrolysis>the amount of addition of fresh enzyme in the secondary hydrolysis; is satisfied, the efficiency of sugar production with respect to the amount of fresh enzyme increases.

The sugar liquid obtained contains monosaccharides such as glucose, xylose, arabinose and mannose derived from cellulose and hemicellulose (xylan and arabinan). The constitution ratios of the monosaccharides are not restricted, and the major monosaccharide components are glucose and xylose. The sugar liquid may also contain oligosaccharides such as cellobiose and the like, although their amounts may be very small compared to the amounts of monosaccharides. The concentration of monosaccharides contained in the sugar liquid is not restricted, and is preferably 0.1 to 20% by weight, more preferably 5 to 20% by weight. In cases where the concentration in the sugar liquid is within the range of 5 to 20% by weight, the sugar liquid can be used as a fermentation feedstock for microorganisms, without being concentrated.

The sugar liquid may be concentrated using a nanofiltration membrane and/or reverse osmosis membrane. Examples of the material of the nanofiltration membrane or reverse osmosis membrane which may be used include polymer materials such as cellulose acetate polymers, polyamides, polyesters, polyimides, vinyl polymers and polysulfones. The membrane is not restricted to a membrane constituted of only one of the materials, and may be a membrane comprising a plurality of membrane materials.

As the nanofiltration membrane to be used, a spiral-wound membrane element is preferred. Specific examples of the preferred nanofiltration membrane element include a cellulose acetate nanofiltration membrane element GE Sepa, manufactured by GE Osmonics; nanofiltration membrane elements NF99 and NF99HF, manufactured by Alfa-Laval, which have polyamide functional layers; nanofiltration membrane elements NF-45, NF-90, NF-200, NF-270 and NF-400, manufactured by FilmTec Corporation, which have cross-linked piperazine polyamide functional layers; and nanofiltration membrane elements SU-210, SU-220, SU-600 and SU-610, manufactured by Toray Industries, Inc., comprising a nanofiltration membrane UTC60, manufactured by the same manufacturer, which comprises a cross-linked piperazine polyamide as a major component. The nanofiltration membrane element is more preferably NF99 or NF99HF; NF-45, NF-90, NF-200 or NF-400; or SU-210, SU-220, SU-600 or SU-610. The nanofiltration membrane element is still more preferably SU-210, SU-220, SU-600 or SU-610.

As the reverse osmosis membrane to be used, a spiral-wound membrane element is preferred as in the case of the nanofiltration membrane. Specific examples of the preferred reverse osmosis membrane element include polyamide reverse osmosis membrane modules manufactured by TORAY INDUSTRIES, INC. SU-710, SU-720, SU-720F, SU-710L, SU-720L, SU-720LF, SU-720R, SU-710P and SU-720P, which are low-pressure type modules, as well as SU-810, SU-820, SU-820L and SU-820FA containing UTC70 as a reverse osmosis membrane, which are high-pressure type modules; cellulose acetate reverse osmosis membranes manufactured by the same manufacturer SC-L100R, SC-L200R, SC-1100, SC-1200, SC-2100, SC-2200, SC-3100, SC-3200, SC-8100 and SC-8200; NTR-759HR, NTR-729HF, NTR-70SWC, ES10-D, ES20-D, ES20-U, ES15-D, ES15-U and LF10-D, manufactured by Nitto Denko Corporation; RO98pHt, RO99, HR98PP and CE4040C-30D, manufactured by Alfa-Laval; GE Sepa, manufactured by GE; and BW30-4040, TW30-4040, XLE-4040, LP-4040, LE-4040, SW30-4040 and SW30HRLE-4040, manufactured by FilmTec Corporation.

The apparatus for carrying out the method for producing a sugar liquid by enzymatic hydrolysis of cellulose is described below more specifically with reference to the accompanying drawings.

As an apparatus mechanism for carrying out the method for producing a sugar liquid, the apparatus comprises: 1. a hydrolysis tank to which a recovered enzyme feed pipe and a fresh enzyme feed pipe are connected; 2. a device for solid-liquid separation of a hydrolysate; 3. a sugar liquid-retaining tank having a water supply pipe for washing an ultrafiltration membrane and/or for removing recovered enzyme retained in a circulation pipe; and 4. an ultrafiltration membrane device for separation of enzyme and a sugar liquid; which are functionally connected to each other. That is, in the method for producing a sugar liquid, the primary hydrolysis is carried out using recovered enzyme. For performing this, 1. the hydrolysis tank to which a recovered enzyme feed pipe and a fresh carbohydrase feed pipe are connected; was provided. Further, for separating the recovered enzyme contained in the hydrolysate, 2. the device for solid-liquid separation of a hydrolysate; and 4. the ultrafiltration membrane device for separation of enzyme and a sugar liquid; were provided. Further, for removing the recovered enzyme liquid and washing the ultrafiltration membrane at the same time, 3. the sugar liquid-retaining tank having a water supply pipe for washing an ultrafiltration membrane and/or for removing recovered enzyme retained in a circulation pipe; was provided. Specific examples of the apparatus are described below with reference to FIGS. 2 to 10.

Figure 2:
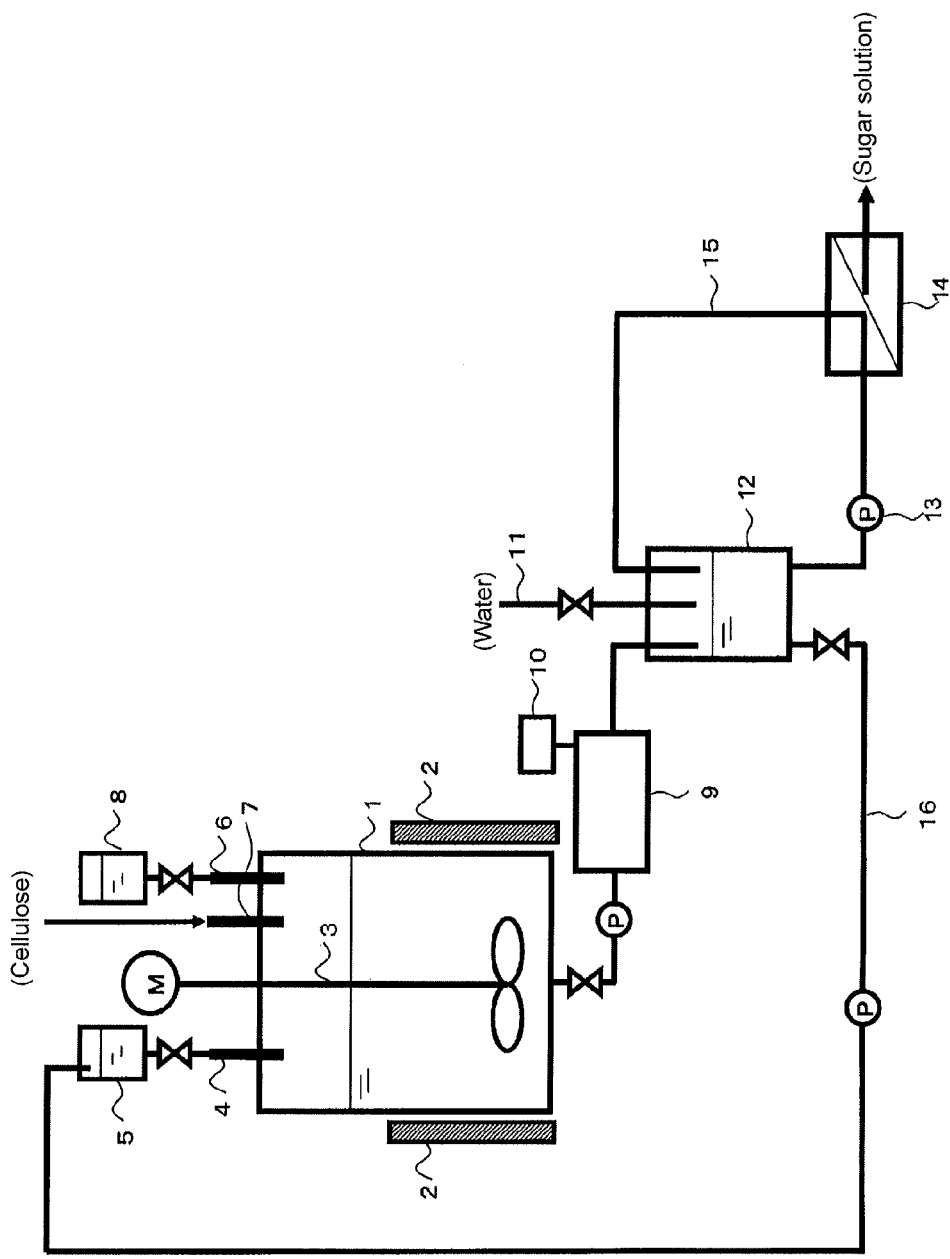
FIG. 2 is a schematic diagram showing an apparatus used in the method.

FIG. 2 shows an example of the apparatus for carrying out the method. That is, the apparatus in FIG. 2 comprises:
a hydrolysis tank 1 having: a recovered enzyme feed pipe 4 that can independently feed the recovered enzyme to the hydrolysis tank and can further control the feeding as required; and a fresh enzyme feed pipe 6 that can independently feed fresh enzyme to the hydrolysis tank and can further control the feeding as required; which are independently connected to the hydrolysis tank 1;

a press filtration device 9 for solid-liquid separation of the hydrolysate;

a sugar liquid-retaining tank 12 having a water supply pipe 11 for washing an ultrafiltration membrane and/or for removing the recovered enzyme retained in a circulation pipe 15; and an ultrafiltration membrane device 14 for separation of the enzyme and the sugar liquid.

Further, for the hydrolysis tank 1, a thermostat 2 for maintaining the temperature during the hydrolysis; a stirring blade 3 for mixing lignocellulose by stirring; and a cellulose inlet 7 were provided. The recovered enzyme feed pipe 4 and the fresh enzyme feed pipe 6 are connected to a recovered enzyme-retaining tank 5 and a fresh enzyme-retaining tank 8, respectively, through valves. Preferably, the valves are separately electronically controlled with pinch valves.

The hydrolysis tank 1 is connected to the press filtration device 9, in which the hydrolysate is separated, through a valve and an air pump or the like, to allow transfer of the hydrolysate into the press filtration device 9. To the press filtration device 9, a compressor 10 for supplying filtration pressure is connected.

The sugar liquid obtained by press filtration is retained in the sugar liquid-retaining tank 12. The sugar liquid-retaining tank 12 is connected to an ultrafiltration membrane device 14 through a circulation pump 13. The recovered enzyme that has passed through the membrane side (feed side) of the ultrafiltration membrane is returned to the sugar liquid-retaining tank 12 through a circulation pipe 15. The sugar solution after removal of the enzyme is collected in the secondary side (permeate side) as a filtrate. The recovered enzyme collected in the sugar liquid-retaining tank 12 is sent to the recovered enzyme-retaining tank 5 through a recovered enzyme pipe 16 and a pump. Water is supplied to the sugar liquid-retaining tank 12 through the water supply pipe 11, and the water is circulated through the ultrafiltration membrane device 14 and the circulation pipe 15 with the circulation pump 13. By this, the recovered enzyme component retained on the surface of the ultrafiltration membrane and in the circulation pipe 15 can be further recovered as a solution, which makes the process efficient. Further, the water-insoluble filamentous fungus-derived cellulase component adhered to the ultrafiltration membrane surface and the like can also be recovered. Further, this circulation of water enables washing of the surface of the ultrafiltration membrane provided in the ultrafiltration membrane device 14, and is useful for suppression of membrane fouling. By this operation, the water retained in the sugar liquid-retaining tank 12 is sent to the recovered enzyme-retaining tank 5 through the recovered enzyme pipe 16. Therefore, the water supplied through the water supply pipe 11 is used for hydrolysis of lignocellulose in the hydrolysis tank 1.

Figure 3:
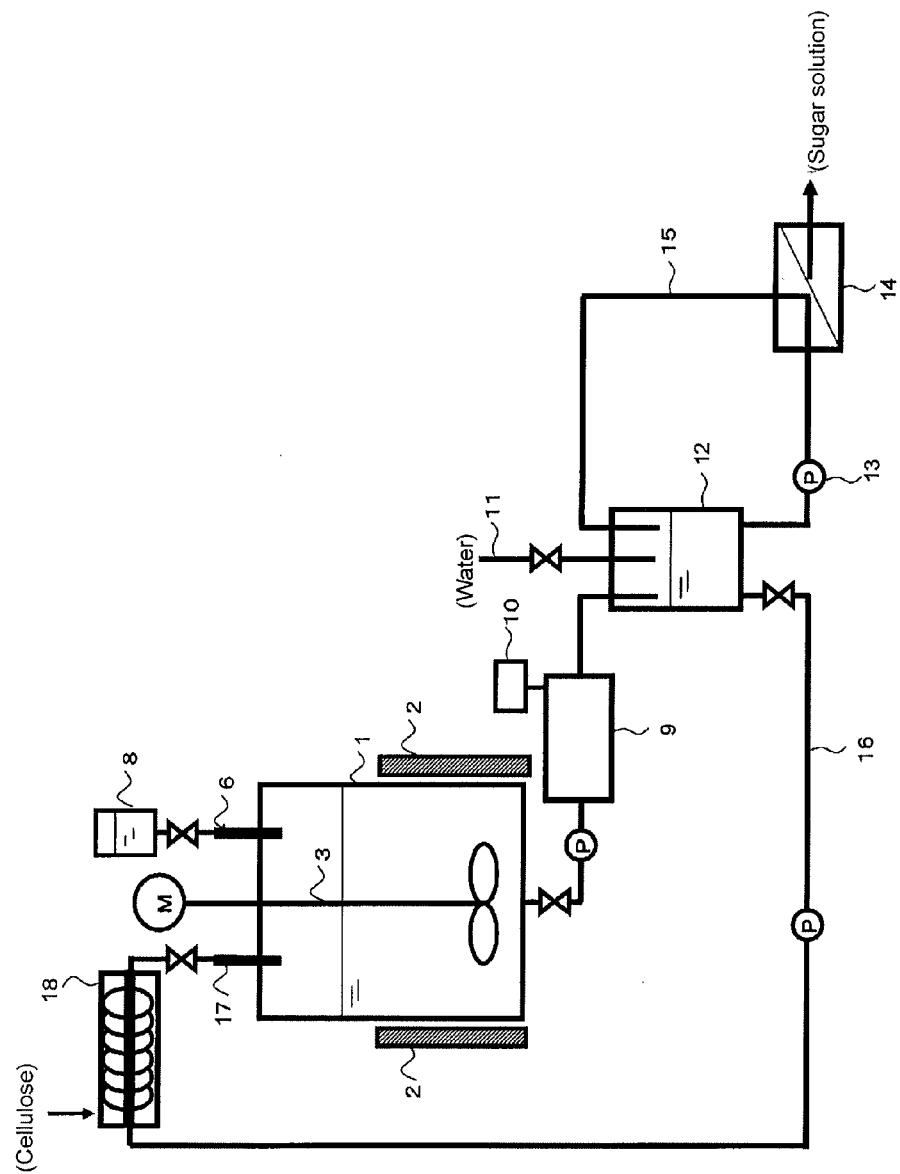
FIG. 3 is a schematic diagram showing an apparatus used in the method.

FIG. 3 shows another example of the apparatus for carrying out the method. That is, the apparatus shown in FIG. 3 comprises:

a cellulose/recovered enzyme-mixing device 18 for mixing the recovered enzyme with cellulose to perform the primary hydrolysis;

a hydrolysis tank 1 having a cellulose/recovered enzyme mixture feed pipe 17 and a fresh enzyme feed pipe 6, which are independently connected to the hydrolysis tank 1;

a press filtration device 9 for solid-liquid separation of the hydrolysate;

a sugar liquid-retaining tank 12 having a water supply pipe 11 for washing an ultrafiltration membrane and/or for removing the recovered enzyme retained in a circulation pipe 15; and an ultrafiltration membrane device 14 for separation of the enzyme and the sugar liquid.

This apparatus is different from the apparatus shown in FIG. 2 in terms of the cellulose/recovered enzyme-mixing device 18 and the inlet 17 provided for the device. The cellulose/recovered enzyme-mixing device 18 is a device for mixing cellulose with the recovered enzyme, and the recovered enzyme is mixed with the cellulose using an internal screw. In the cellulose/recovered enzyme-mixing device 18, the primary hydrolysis of Step (1) is carried out. The cellulose/recovered enzyme-mixing device 18 may be kept at a temperature suitable for the primary hydrolysis. Further, the recovered enzyme may be preliminarily incubated, followed by being mixed with cellulose in the cellulose/recovered enzyme-mixing device 18 to perform the primary hydrolysis. By preliminarily mixing the recovered enzyme with cellulose in the cellulose/recovered enzyme-mixing device 18, the cost of the power required for stirring the mixture in the hydrolysis tank 1 can be reduced. Further, by preliminarily mixing the recovered enzyme with cellulose in the cellulose/recovered enzyme-mixing device 18, the length of time required for evenly dispersing cellulose in the hydrolysis tank 1 can be shortened, which results in shortening of the length of time required for the hydrolysis. The primary hydrolysate obtained in the cellulose/recovered enzyme-mixing device 18 is fed to the hydrolysis device 1 through the cellulose/recovered enzyme mixture supply pipe 17. Thereafter, the fresh enzyme containing filamentous fungus-derived cellulase of Step (2) is added from the fresh enzyme feed pipe 6 to perform the secondary hydrolysis. The subsequent solid-liquid separation and the operation of enzyme recovery are the same as those for the apparatus shown in FIG. 2.

Figure 4:
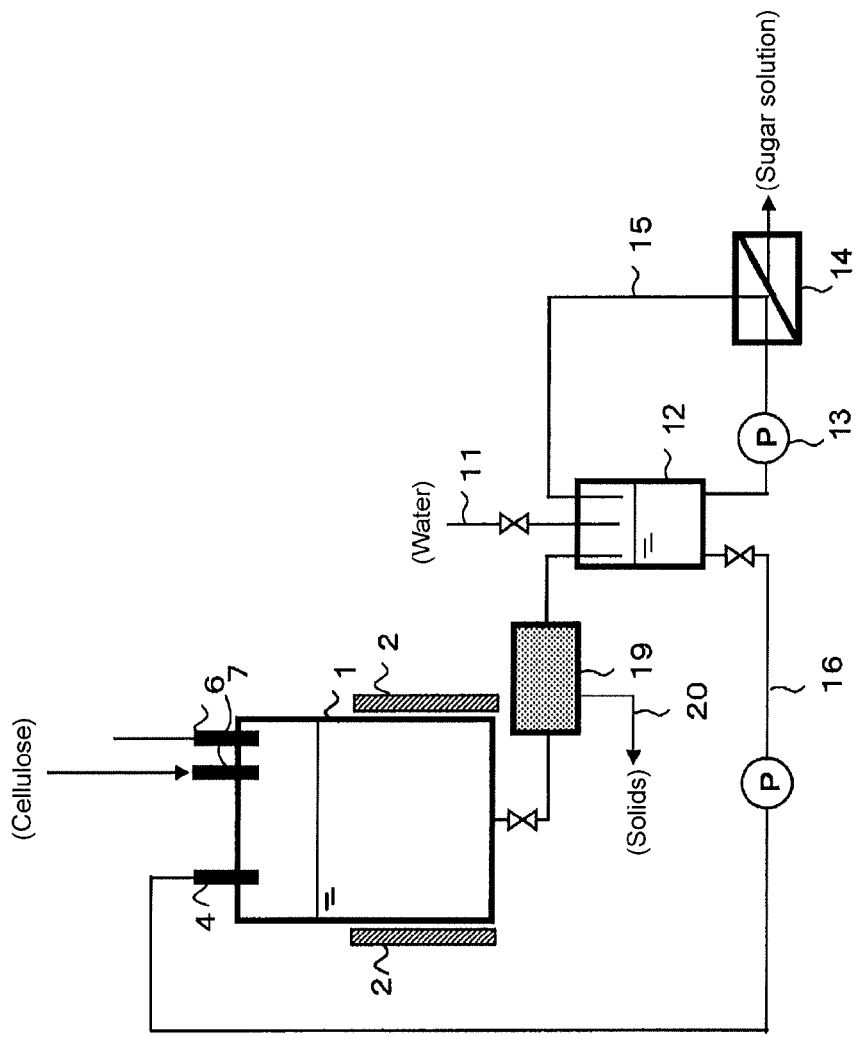
FIG. 4 is a schematic diagram showing an apparatus used in the method.

FIG. 4 shows another example of the apparatus for carrying out the method. The apparatus shown in FIG. 4 corresponds to the case where a solid-liquid separation device 19 comprising a filter press is employed for the above-described apparatus shown in FIG. 2. The recovered enzyme-retaining tank 5, fresh enzyme-retaining tank 8 and stirring blade 3 described in FIG. 2 are not shown in FIG. 4 since these may be provided as required. The solids separated by the solid-liquid separation device 19 are removed through a solids discharge pipe 20. The solid-liquid separation device 19 may be a filter press as shown in FIGS. 2 and 3 above, and examples of other solid-liquid separation devices include a continuous centrifuge, screw decanter, De Laval centrifuge, screw press, belt filter and drum filter. In terms of the basic characteristics of the apparatus, the hydrolysis tank has a recovered enzyme feed pipe 4 and a fresh enzyme feed pipe 6 which are independently connected thereto and therefore allow independent control of addition of the recovered enzyme and addition of fresh enzyme, and the sugar liquid-retaining tank 12 has a water supply pipe 11 connected thereto such that water supplied from the water supply pipe 11 can be circulated into an ultrafiltration membrane device 14 and can also be supplied through a recovered enzyme pipe 16 into the hydrolysis tank 1. These characteristics are the same as those of the apparatuses shown in FIGS. 2 and 3.

Figure 5:
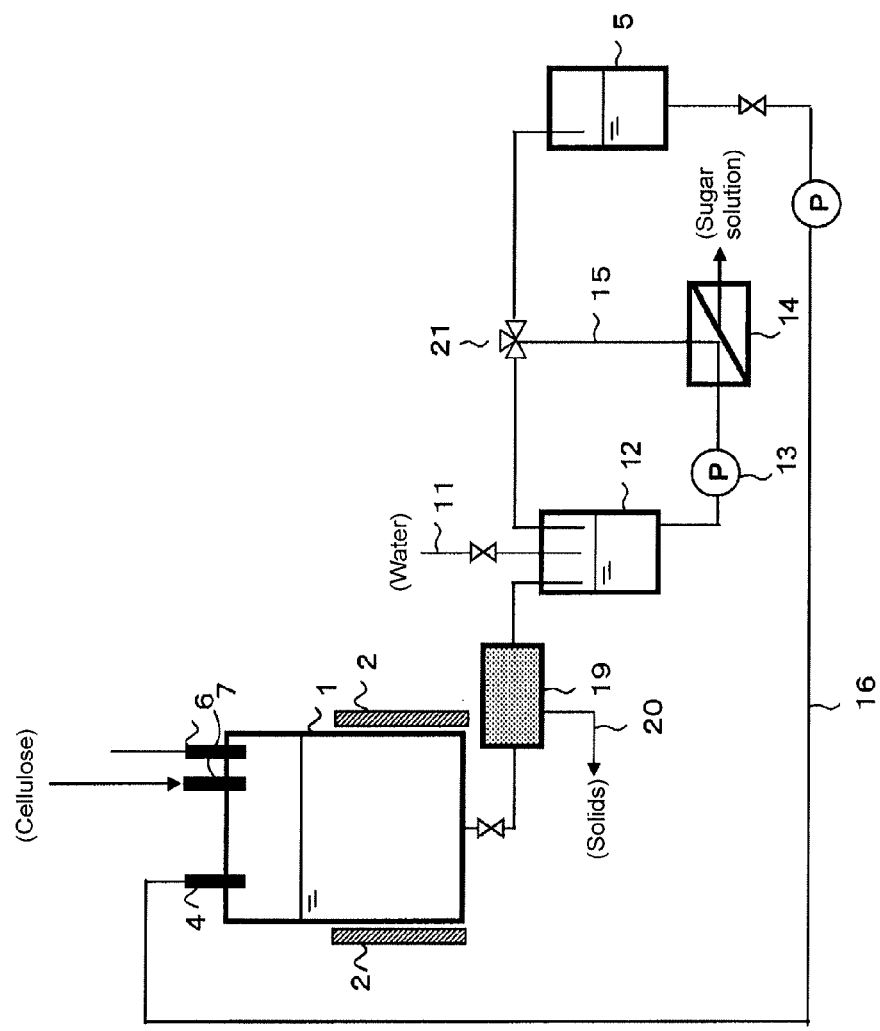
FIG. 5 is a schematic diagram showing an apparatus used in the method.

FIG. 5 shows another example of the apparatus for carrying out the method. The apparatus shown in FIG. 5 is basically the same as the above-described apparatus in FIG. 4, but the non-permeated-liquid side of the ultrafiltration membrane 14 is connected to the recovered enzyme-retaining tank 5. This apparatus particularly uses, as the ultrafiltration membrane, spiral elements that are connected linearly or in a tree-shaped manner. In this apparatus, similarly to the apparatuses shown in FIGS. 2 to 4, a water supply pipe 11 is connected to a sugar liquid-retaining tank 12. Water supplied through the water supply pipe 11 can be circulated into the ultrafiltration membrane device 14 by switching of piping using a three-way valve 21, and further switching using the three-way valve 21 allows the water to be supplied into a recovered enzyme-retaining tank 5. Further, a recovered enzyme pipe 16 is connected to the recovered enzyme-retaining tank 5, and, through this pipe, the water can be supplied into the hydrolysis tank 1. Similarly to the apparatuses shown in FIGS. 2 to 4, a recovered enzyme feed pipe 4 and a fresh enzyme feed pipe 6 are independently connected to the hydrolysis tank, allowing independent control of addition of the recovered enzyme and addition of fresh enzyme.

Figure 6:
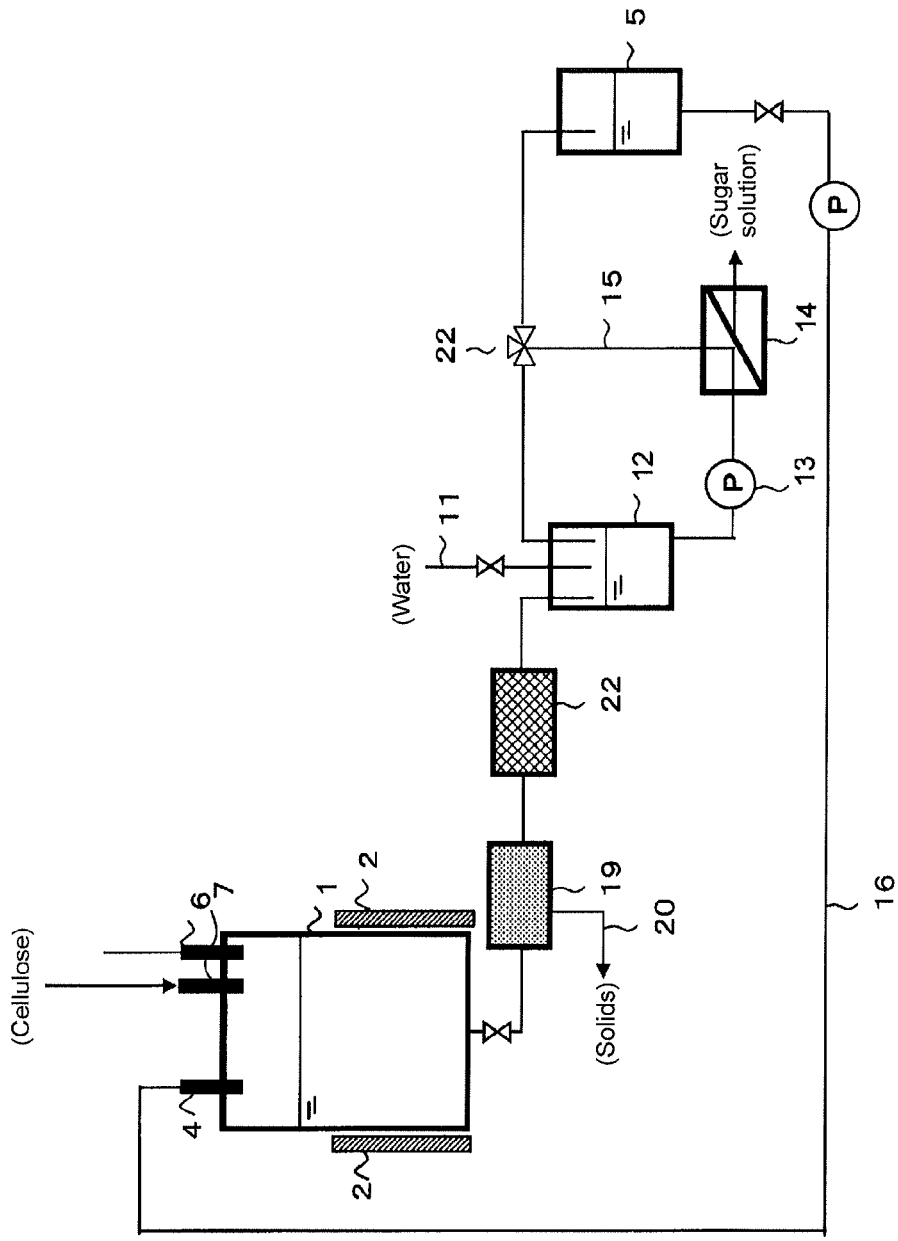
FIG. 6 is a schematic diagram showing an apparatus used in the method.

FIG. 6 shows another example of the apparatus for carrying out the method. In the apparatus shown in FIG. 6, a microfiltration membrane device 22 is placed downstream of a solid-liquid separation device 19. In cases where solids cannot be sufficiently removed in the solid-liquid separation device 19, further processing with the microfiltration membrane device 22 allows production of a liquid that is almost completely free from solids. By this, membrane fouling of the ultrafiltration membrane device 14 can be reduced in a later step.

Figure 7:
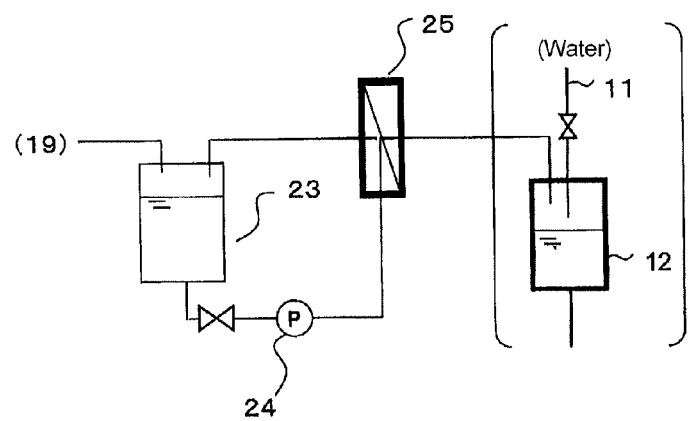
FIG. 7 is a schematic diagram showing an apparatus used in the method.

FIG. 7 is a detailed drawing of the microfiltration membrane device 22 shown in FIG. 6, and shows a constitution of the device for performing cross-flow filtration. In this device, the filtrate separated by the solid-liquid separation device 19 is retained in a solid-liquid separation filtrate tank 23, and cross-flow filtration is performed in a microfiltration membrane 25 connected through a pump 24. The microfiltration membrane 25 may be in the form of either a flat membrane or hollow-fiber membrane. The hollow fiber membrane may be either an internal-pressure type membrane or an external-pressure type membrane.

Figure 8:
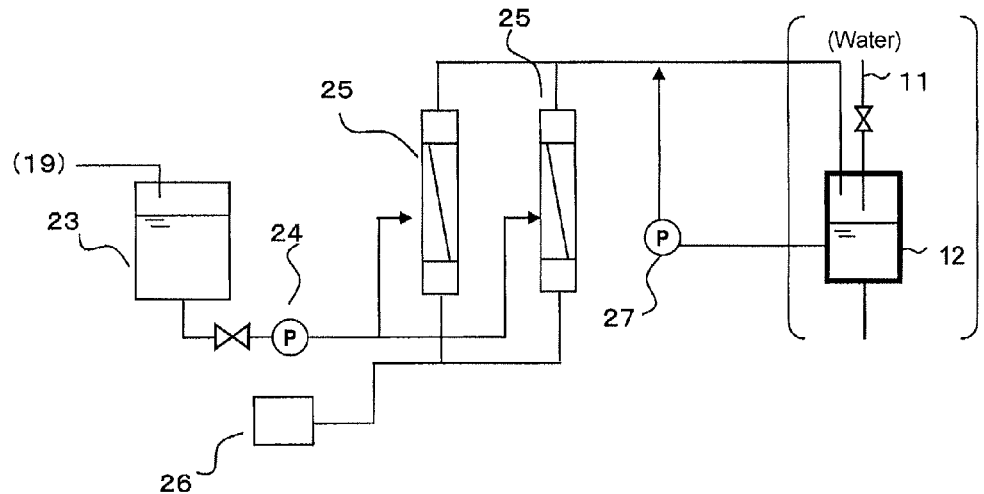
FIG. 8 is a schematic diagram showing an apparatus used in the method.

FIG. 8 is a detailed drawing of the microfiltration membrane device 22 shown in FIG. 6, and shows a constitution of the device for performing dead-end filtration in the microfiltration membrane device 22. The filtrate separated by the solid-liquid separation device 19 is retained in a solid-liquid separation filtrate retaining tank 23, and filtered through a microfiltration membrane 25. In cases of dead-end filtration, a compressed-air supply device 26 for performing air-bubble washing of the membrane surface may be provided, and a reverse-washing pump 27 for reverse washing may be placed. The reverse washing may be carried out either with the filtrate recovered into the sugar liquid-retaining tank 12 or with a common membrane washing liquid or liquid agent. The microfiltration membrane 25 may be in the form of either a flat membrane or hollow fiber membrane. The hollow fiber membrane may be either an internal-pressure type membrane or an external-pressure type membrane.

Figure 9:
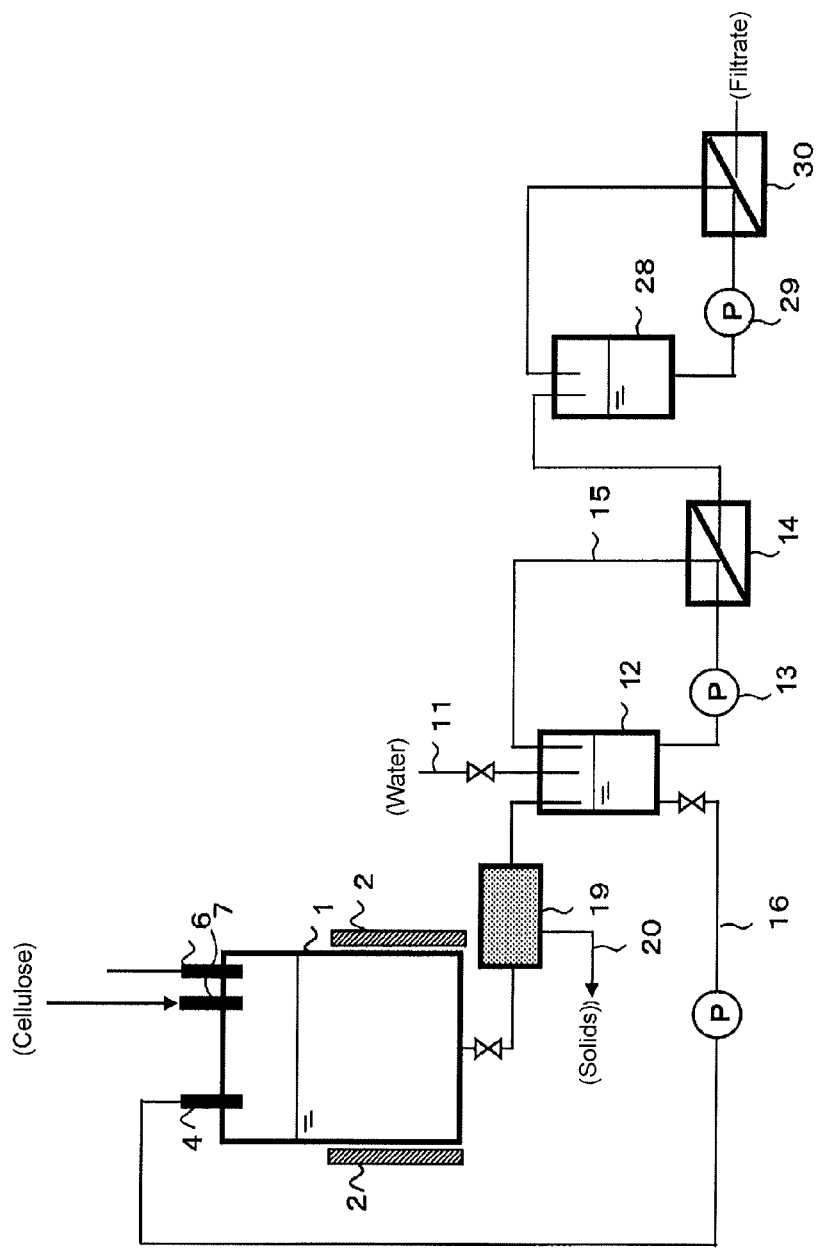
FIG. 9 is a schematic diagram showing an apparatus used in the method.

FIG. 9 shows another example of the apparatus for carrying out the method. The apparatus for producing a sugar liquid may further have a reverse osmosis membrane and/or nanofiltration membrane to concentrate the sugar liquid. FIG. 9 shows a apparatus corresponding to the apparatus shown in FIG. 4 to which a nanofiltration membrane or reverse osmosis membrane device 30 is further connected. To the filtrate side of the ultrafiltration membrane device 14, a sugar liquid concentrating tank 28 is further connected, and filtration is performed with a reverse osmosis membrane and/or nanofiltration membrane 30 through a high-pressure pump 29. The sugar liquid is blocked by the reverse osmosis membrane and/or nanofiltration membrane and therefore concentrated in the sugar liquid concentrating tank 28. On the other hand, excess water can be removed as the filtrate. The reverse osmosis membrane and/or nanofiltration membrane device 30 can be placed by being connected to the filtrate side of the ultrafiltration membrane device 14 in any of the apparatuses shown in FIGS. 2 to 6.

Figure 10:
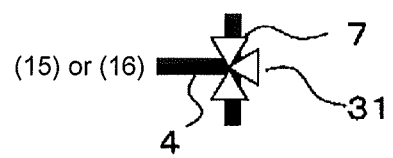
FIG. 10 is a schematic diagram showing an apparatus used in the method.

FIG. 10 shows another example of the apparatus for carrying out the method. The recovered enzyme feed pipe 4 and the fresh enzyme feed pipe 6 are preferably independently connected to the hydrolysis tank 1, but the pipe 4 and the pipe 6 may be joined to each other at a three-way valve 31 or the like to form a single pipe (fresh enzyme or recovered enzyme feed pipe) connected to the hydrolysis tank 1, as long as feeding of each of the enzyme components can be controlled thereby.

The water supplied from the water supply pipe 11 may be warm water. The temperature of the warm water is preferably not higher than 60° C. in view of prevention of inactivation of the enzyme. By supplying warm water from the water supply pipe, and allowing the warm water to circulate into the ultrafiltration membrane device 14, a high washing effect can be obtained for the ultrafiltration membrane. For a higher washing effect, the temperature of the warm water is preferably 30° C. to 60° C.

EXAMPLES

Our methods and apparatus are described below more specifically by way of Examples. However, this disclosure is not restricted to these Examples.

Reference Example 1

Preparation of Cellulase (*Trichoderma*-Derived Cellulase Enzyme Composition)

An enzyme composition derived from a culture liquid of *Trichoderma* was prepared by the following method.
Preculture
The mixture of 5% corn steep liquor (w/vol), 2% glucose (w/vol), 0.37% ammonium tartrate (w/vol), 0.14 (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid and 0.0026% (w/vol) hexaammonium heptamolybdate tetrahydrate in distilled water was prepared, and 100 mL of this mixture was placed in a baffled 500-mL Erlenmeyer flask, followed by being sterilized by autoclaving at 121° C. for 15 minutes. After allowing the mixture to cool, PE-M and Tween 80, each of which was sterilized by autoclaving at 121° C. for 15 minutes separately from the mixture, were added thereto at 0.01% (w/vol) each. To this preculture medium, *Trichoderma reesei* ATCC68589 was inoculated at $1 \times 10^5$ cells/mL, and the cells were cultured at 28° C. for 72 hours with shaking at 180 rpm, to perform preculture (shaker: BIO-SHAKER BR-40LF, manufactured by TAITEC CORPORATION).
Main Culture
The mixture of 5% corn steep liquor (w/vol), 2% glucose (w/vol), 10% (w/vol) cellulose (Avicel), 0.37% ammonium tartrate (w/vol), 0.14% (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid and 0.0026% (w/vol) hexaammonium heptamolybdate tetrahydrate in distilled water was prepared, and 2.5 L of this mixture was placed in a 5-L stirring jar (manufactured by ABLE, DPC-2A), followed by being sterilized by autoclaving at 121° C. for 15 minutes. After allowing the mixture to cool, PE-M and Tween 80, each of which was sterilized by autoclaving at 121° C. for 15 minutes separately from the mixture, were added thereto at 0.1% each. To the resulting mixture, 250 mL of preculture of *Trichoderma reesei* ATCC68589 preliminarily prepared with a liquid medium by the method described above was inoculated. The cells were cultured at 28° C. for 87 hours at 300 rpm at an aeration rate of 1 vvm. After centrifugation, the supernatant was subjected to membrane filtration (Stericup-GV, manufactured by Millipore, material: PVDF). To the culture liquid prepared under the above-described conditions, β-glucosidase (Novozyme 188) was added at a protein weight ratio of 1/100, and the resulting mixture was used as *Trichoderma*-derived cellulase in the Examples below.

Reference Example 2

Preparation of Pretreated Cellulase

Preparation of Pretreated Cellulose 1
Avicell (manufactured by Merck), which is commercially available, was used as the pretreated cellulose 1 in the Examples below, without performing any treatment.
Preparation of Pretreated Cellulose 2
As a cellulose-containing biomass, rice straw was used. The cellulose-containing biomass was soaked in 1% aqueous sulfuric acid solution, and subjected to treatment using an autoclave (manufactured by Nitto Koatsu Co., Ltd.) at 150° C. for 30 minutes. Thereafter, solid-liquid separation was carried out to separate sulfuric acid-treated cellulose from the aqueous sulfuric acid solution (hereinafter referred to as "dilute-sulfuric-acid treatment liquid"). Subsequently, the sulfuric acid-treated cellulose was mixed with the dilute-sulfuric-acid treatment liquid with stirring such that the concentration of the solid contents is 10% by weight, and the pH was adjusted to about 5 with sodium hydroxide. The resulting mixture was used in the Examples below as the pretreated cellulose 2.
Preparation of Pretreated Cellulose 3
As the cellulose, rice straw was used. The cellulose-containing biomass was fed into a compact reactor (manufactured by Taiatsu Techno Corporation, TVS-N2 30 ml), and cooled with liquid nitrogen. Into this reactor, ammonia gas was flown, and the sample was completely soaked in liquid ammonia. The lid of the reactor was closed, and the reactor was left to stand at room temperature for about 15 minutes. Subsequently, the reactor was processed in an oil bath at 150° C. for 1 hour. Thereafter, the reactor was removed from the oil bath, and the ammonia gas was leaked in a fume hood, followed by vacuuming the inside of the reactor to 10 Pa with a vacuum pump, thereby drying the cellulose. The resultant was used in the Examples below as the pretreated cellulose 3.
Preparation of Pretreated Cellulose 4
As a cellulose-containing biomass, rice straw was used. The cellulose-containing biomass was soaked in water, and subjected to treatment using an autoclave (manufactured by Nitto Koatsu Co., Ltd.) at 180° C. for 20 minutes with stirring. The treatment was carried out at a pressure of 10 MPa. After the treatment, solid-liquid separation was carried out by centrifugation (3000 G) to separate the processed biomass component from the solution component (hereinafter referred to as "hydrothermally treated liquid"). This was used in the Examples below as the pretreated cellulose 4.

Reference Example 3

Measurement of Sugar Concentration

The concentrations of glucose and xylose contained in the aqueous sugar solution were measured under the HPLC conditions described below based on comparison with standard samples:
Column: Luna $NH_2$ (manufactured by Phenomenex, Inc.)
Mobile phase: MilliQ:acetonitrile=25:75 (flow rate, 0.6 mL/minute)
Reaction solution: None
Detection method: RI (differential refractive index)
Temperature: 30° C.

Reference Example 4

Measurement of Enzyme Activity of *Trichoderma*-Derived Cellulase

The enzyme activity of the *Trichoderma*-derived cellulase was measured by the following procedure.
1) Crystalline Cellulose-Degrading Activity
To an enzyme liquid (prepared under predetermined conditions), Avicel (manufactured by Merck . . . this needs to be confirmed) was added at 1 g/L and sodium acetate buffer (pH 5.0) was added at 100 mM, followed by allowing the resulting mixture to react at 50° C. for 24 hours. This reaction liquid was prepared in a 1-mL tube, and the reaction was allowed to proceed with mixing by rotation under the above-described conditions. Thereafter, the tube was subjected to centrifugation, and the glucose concentration in the supernatant component was measured. The measurement of the glucose concentration was carried out according to the method described in Reference Example 3. The concentration of the produced glucose (g/L) was used as it is as the activity value of the Avicel-degrading activity.
2) Cellobiose-Degrading Activity
To an enzyme liquid, cellobiose (Wako Pure Chemical Industries, Ltd.) was added at 500 mg/L and sodium acetate buffer (pH 5.0) was added at 100 mM, followed by allowing the resulting mixture to react at 50° C. for 0.5 hour. This reaction liquid was prepared in a 1-mL tube, and the reaction was allowed to proceed with mixing by rotation under the above-described conditions. Thereafter, the tube was subjected to centrifugation, and the glucose concentration in the supernatant component was measured. The measurement of the glucose concentration was carried out according to the method described in Reference Example 3. The concentration of the produced glucose (g/L) was used as it is as the activity value of the cellobiose-degrading activity.
3) Xylan-Degrading Activity
To an enzyme liquid, xylan (Birch wood xylan, Wako Pure Chemical Industries, Ltd.) was added at 10 g/L and sodium acetate buffer (pH 5.0) was added at 100 mM, followed by allowing the resulting mixture to react at 50° C. for 4 hours. This reaction liquid was prepared in a 1-mL tube, and the reaction was allowed to proceed with mixing by rotation under the above-described conditions. Thereafter, the tube was subjected to centrifugation, and the xylose concentration in the supernatant component was measured. The measurement of the xylose concentration was carried out according to the method described in Reference Example 3. The concentration of the produced xylose (g/L) was used as it is as the activity value of the xylose-degrading activity.

Comparative Example 1

As a Comparative Example, a sugar liquid was produced from cellulose as described below without performing either the primary hydrolysis or secondary hydrolysis.

Step 1: Hydrolysis

To each of the pretreated celluloses 1 to 4 (1 g each), 0.2 mL (amount of protein, 10 mg) of the fresh enzyme described in Reference Example 1 (protein concentration, 50 mg/mL) was added, and the solution of enzyme recovered by the procedure which is described later in Step 2 was further added. Distilled water was further added such that the weight of the resulting solution became 10 g. The composition was transferred to a side-arm reactor ($\phi$30 NS14/23, manufactured by Tokyo Rikakikai Co., Ltd.), followed by performing hydrolysis at 50° C. for 19 hours with incubation and stirring (compact mechanical stirrer CPS-1000, manufactured by Tokyo Rikakikai Co., Ltd., conversion adapter, feed inlet with a three-way stopcock, incubator MG-2200).

Step 2: Solid-Liquid Separation and Recovery of Enzyme (Recovered Enzyme) from Sugar Liquid The hydrolysate in Step 1 was subjected to solid-liquid separation by centrifugation (4500 G, 10 minutes), and separated into a sugar liquid and the residue. The glucose and xylose concentrations in the sugar liquid were measured by the method described in Reference Example 3, and calculated as produced sugars.

The sugar liquid was further subjected to membrane filtration (Steriflip-GP, manufactured by Millipore, material: PES). The obtained supernatant was applied to an ultrafiltration membrane having a molecular weight cutoff of 10000 (VIVASPIN 20, manufactured by Sartorius stedim biotech, material: PES) and centrifuged at 4500 G until the membrane fraction was reduced to 1 mL. To the membrane fraction, 10 mL of distilled water was added, and the resulting mixture was centrifuged again at 4500 G until the membrane fraction was reduced to 1 mL. Thereafter, the enzyme was recovered from the membrane fraction to provide a recovered enzyme. The recovered enzyme was reused for the hydrolysis in Step 1 as described above.

In the Comparative Example, Step 1 and Step 2 were carried out in rotation to recover and reuse cellulase. The cycle constituted by Step 1 and Step 2 was repeated a total of 6 times to carry out the recovery and reuse. The 0th reaction, wherein the recovery and reuse were not carried out, was performed by the following procedure.

Step 0: 0th Hydrolysis

To each of the pretreated celluloses 1 to 4 (1 g each), 0.3 mL (amount of protein, 15 mg) of fresh enzyme (protein concentration, 50 mg/mL) was added (recovered enzyme was not added since this was the 0th hydrolysis). Distilled water was further added such that the weight of the resulting solution became 10 g. The composition was transferred to a side-arm reactor ($\phi$30 NS14/23, manufactured by Tokyo Rikakikai Co., Ltd.), followed by performing hydrolysis at 50° C. for 19 hours with incubation and stirring (compact mechanical stirrer CPS-1000, manufactured by Tokyo Rikakikai Co., Ltd., conversion adapter, feed inlet with a three-way stopcock, incubator MG-2200). By separation of the obtained hydrolysate by the method described in the above Step 2, a recovered enzyme was obtained. The glucose and xylose concentrations in the sugar liquid at this time were measured.

Table 1 summarizes the glucose concentrations (Glc, g/L) and xylose concentrations (Xly, g/L) in the sugar liquids obtained by the reactions wherein Step 0 and 2 were carried out once and Steps 1 and 2 were carried out in order a total of 6 times. As the number of times of recovery and reuse increased, glucose (Glc) and xylose (Xyl) decreased. Further, it was revealed that the sugar production efficiency gradually decreases as the number of times of reuse (N) increases.

TABLE 1

| | | 0th hydrolysis | 1st hydrolysis | 2nd hydrolysis | 3rd hydrolysis | 4th hydrolysis | 5th hydrolysis | 6th hydrolysis |
|---|---|---|---|---|---|---|---|---|
| Pretreated cellulose 1 | Glc | 42 | 39 | 37 | 35 | 31 | 30 | 27 |
| | Xyl | 1 | 0.8 | 0.7 | 0.6 | 0.4 | 0.4 | 0.3 |
| Pretreated cellulose 2 | Glc | 32 | 30 | 28 | 27 | 25 | 23 | 20 |
| | Xyl | 7 | 4 | 3 | 2 | 0.9 | 0.6 | 0.3 |
| Pretreated cellulose 3 | Glc | 40 | 35 | 31 | 28 | 25 | 24 | 22 |
| | Xyl | 12 | 10 | 9 | 7 | 6 | 4 | 4 |
| Pretreated cellulose 4 | Glc | 25 | 23 | 22 | 20 | 18 | 18 | 15 |
| | Xyl | 4 | 2 | 2 | 1 | 0.4 | 0.2 | 0.1 |

Example 1

As an Example, cellulose was subjected to the primary hydrolysis and the secondary hydrolysis as described below, to produce a sugar liquid.

Step 1: Primary Hydrolysis

To each of the pretreated celluloses 1 to 4 (1 g each), distilled water was added, and a recovered enzyme which was recovered by the later-mentioned procedure of Step 3 was added, followed by further adding distilled water such that the total weight became 10 g. The composition was transferred to a side-arm reactor ($\phi$30 NS14/23, manufactured by Tokyo Rikakikai Co., Ltd.), followed by performing hydrolysis at 50° C. for 1 hour with incubation and stirring (compact mechanical stirrer CPS-1000, manufactured by Tokyo Rikakikai Co., Ltd., conversion adapter, feed inlet with a three-way stopcock, incubator MG-2200).

Step 2: Secondary Hydrolysis

To the primary hydrolysate in Step 1, 0.2 mL (amount of protein, 10 mg) of the fresh enzyme described in Reference Example 1 (protein concentration, 50 mg/mL) was added, and the reaction was allowed to proceed at 50° C. for 18 hours.

Step 3: Solid-Liquid Separation and Recovery of Enzyme (Recovered Enzyme) from Sugar Liquid The secondary hydrolysate in Step 3 was subjected to solid-liquid separation by centrifugation (4500 G, 10 minutes), and separated into a sugar liquid and the residue. The glucose and xylose concentrations in the sugar liquid were measured by the method described in Reference Example 3, and calculated as the Nth produced sugars. The sugar liquid was further subjected to membrane filtration (Steriflip-GP, manufactured by Millipore, material: PES), and the obtained supernatant was applied to an ultrafiltration membrane having a molecular weight cutoff of 10000 (VIVASPIN 20, manufactured by Sartorius stedim biotech, material: PES) and centrifuged at 4500 G until the membrane fraction was reduced to 1 mL. To the membrane fraction, 10 mL of distilled water was added, and the resulting mixture was centrifuged again at 4500 G until the membrane fraction was reduced to 1 mL. Thereafter, the enzyme was recovered from the membrane fraction to provide a recovered enzyme. The recovered enzyme was reused for the hydrolysis in Step 1 as described above.

In the Example, Step 1 to Step 3 were carried out in rotation to recover and reuse cellulase. The cycle constituted by Steps 1 to 3 was repeated a total of 6 times to carry out the recovery and reuse. The 0th reaction, wherein the recovery and reuse were not carried out, was performed by the following procedure.

Step 0: 0th Hydrolysis

To each of the pretreated celluloses 1 to 4 (1 g each), 0.3 mL (amount of protein, 15 mg) of fresh enzyme (protein concentration, 50 mg/mL) was added (recovered enzyme was not added since this was the 0th hydrolysis). Distilled water was further added such that the weight of the resulting solution became 10 g. The composition was transferred to a side-arm reactor (ϕ30 NS14/23, manufactured by Tokyo Rikakikai Co., Ltd.), followed by performing hydrolysis at 50° C. for 19 hours with incubation and stirring (compact mechanical stirrer CPS-1000, manufactured by Tokyo Rikakikai Co., Ltd., conversion adapter, feed inlet with a three-way stopcock, incubator MG-2200). By separation of the obtained hydrolysate by the method described in the above Step 3, a recovered enzyme was obtained. The glucose and xylose concentrations in the sugar liquid at this time were measured.

Table 2 summarizes the glucose concentrations (Glc) (g/L) and xylose concentrations (Xly) (g/L) in the sugar liquids obtained by the reactions wherein Step 0 and 3 were carried out once and Steps 1 to 3 were carried out in order a total of 6 times. As the number of times of recovery and reuse increased, glucose (Glc) and xylose (Xyl) decreased. However, it could be confirmed that the amount of sugar production gradually increases by contrast to the cases in Reference Example 1 (Table 1).

In the Example, the primary hydrolysis with the recovered enzyme was performed for 1 hour, and the secondary hydrolysis after addition of fresh enzyme was performed for 18 hours, by which the hydrolysis reaction was carried out for 19 hours as in Comparative Example 1. Further, the amount of addition of fresh enzyme was the same as in Comparative Example 1. Therefore, in the Example, it was shown that, by carrying out in rotation the steps of: 1. adding the recovered enzyme to the pretreated cellulose to perform the primary hydrolysis; 2. adding fresh enzyme to the hydrolysate to perform the secondary hydrolysis; and 3. subjecting the hydrolysate to solid-liquid separation to obtain the recovered enzyme from the obtained sugar liquid; the concentration of the sugar obtained by the recovery and reuse, that is, the sugar production efficiency, can be higher than that in the Comparative Example.

Example 2

Measurement of Amount of Addition of Recovered Enzyme in Primary Hydrolysis

The protein concentration of the recovered enzyme to be added for the primary hydrolysis in Example 1 was assayed with the BCA measurement kit (BCA Protein Assay Reagent kit, manufactured by PIERCE), using bovine albumin (2 mg/mL) as a standard sample, by measurement of the absorbance at 562 nm to perform colorimetry. Table 3 summarizes, in terms of the recovery/reuse of the enzyme for the pretreated cellulose 2, the relationship between the amount of recovered enzyme obtained by the Nth recovery and the amount of addition of fresh enzyme. Taking the amount of glucose production summarized in Table 2 in Example 1 into account, it could be confirmed by the present Example that the amount of production of glucose can be further increased if the relationship: the amount of addition of enzyme in the primary hydrolysis>the amount of addition of enzyme in the secondary hydrolysis; and further, the relationship: the amount of recovered enzyme reused for the primary hydrolysis>the amount of fresh enzyme added for the secondary hydrolysis; are satisfied, as in the cases of the 4th and later recovery/reuse.

TABLE 2

| | | 0th hydrolysis | 1st hydrolysis | 2nd hydrolysis | 3rd hydrolysis | 4th hydrolysis | 5th hydrolysis | 6th hydrolysis |
|---|---|---|---|---|---|---|---|---|
| Sugar Concentration (g/L) in Pretreated cellulose 1 | Glc | 42 | 42 | 43 | 45 | 47 | 48 | 49 |
| | Xyl | 1 | 1 | 1 | 1 | 1.1 | 1.1 | 1.2 |
| Sugar Concentration (g/L) in Pretreated cellulose 2 | Glc | 32 | 32 | 33 | 33 | 34 | 36 | 39 |
| | Xyl | 7 | 6 | 6 | 7 | 8 | 9 | 10 |
| Sugar Concentration (g/L) in Pretreated cellulose 3 | Glc | 32 | 30 | 33 | 34 | 35 | 38 | 40 |
| | Xyl | 7 | 6 | 6 | 7 | 8 | 10 | 11 |
| Sugar Concentration (g/L) in Pretreated cellulose 4 | Glc | 25 | 24 | 24 | 25 | 25 | 26 | 26 |
| | Xyl | 4 | 3 | 3 | 3 | 3 | 5 | 5 |

TABLE 3

|  | 0th hydrolysis | 1st hydrolysis | 2nd hydrolysis | 3rd hydrolysis | 4th hydrolysis | 5th hydrolysis | 6th hydrolysis |
|---|---|---|---|---|---|---|---|
| Amount of protein in recovered enzyme (mg) | — | 7 | 8.4 | 9.3 | 11 | 12 | 14 |
| Amount of protein in fresh enzyme (mg) | 15 | 10 | 10 | 10 | 10 | 10 | 10 |
| Glucose Concentration in pretreated cellulose 2 (g/L) | 32 | 32 | 33 | 33 | 34 | 36 | 39 |

Example 3

Enzyme Activity of Recovered Enzyme

The activity of the recovered enzyme was measured for cases of the pretreated cellulose 3 (Comparative Example 1: the case where the recovered enzyme was fed at the same time with fresh enzyme; Example 1: the case where the recovered enzyme was added to perform the primary hydrolysis, after which fresh enzyme was fed). The enzyme activity was measured according to Reference Example 3 for 3 types of degradation activities, that is, 1) crystalline cellulose-degrading activity, 2) cellobiose-degrading activity, and 3) xylan-degrading activity. Each degradation activity was expressed as a relative value (%) of the enzyme activity in the recovered enzyme, taking the enzyme activity of the fresh enzyme (10 mg) as 100 (%). The activities of the recovered enzymes after the 2nd recovery and the 4th recovery are shown in Table 4 (Example 1) and Table 5 (Comparative Example 1).

TABLE 4

|  | Fresh enzyme (10 mg) | Recovered enzyme | |
|---|---|---|---|
|  |  | 2nd hydrolysis | 4th hydrolysis |
| Crystalline cellulose-degrading activity | 100 | 84 | 110 |
| Cellobiose-degrading activity | 100 | 94 | 114 |
| Xylan-degrading activity | 100 | 154 | 250 |

TABLE 5

|  | Fresh enzyme (10 mg) | Recovered enzyme | |
|---|---|---|---|
|  |  | 2nd hydrolysis | 4th hydrolysis |
| Crystalline cellulose-degrading activity | 100 | 74 | 80 |
| Cellobiose-degrading activity | 100 | 80 | 84 |
| Xylan-degrading activity | 100 | 114 | 106 |

It was revealed that, as the number of times of the primary hydrolysis increases, all of the crystalline cellulose-degrading activity, cellobiose-degrading activity and xylan-degrading activity tend to increase, and such a tendency is especially remarkable in the xylan-degrading activity. Since especially Trichoderma-derived xylanase and xylosidase are involved in the xylan-degrading activity, it is thought that the efficiency of recovery of these enzymes has increased as the number of times of the primary hydrolysis increased.

Example 4

Aggregated Trichoderma-Derived Cellulase Component Contained in Recovered Enzyme It was found that, in the 4th and later recovery, a water-insoluble component is produced in the recovered enzyme component that is recovered as a non-permeated liquid of the ultrafiltration membrane. This water-insoluble Trichoderma-derived cellulase component was analyzed by the following procedure.

Using the pretreated cellulose 3, the primary hydrolysis and the secondary hydrolysis were carried out by the procedure in Example 1, and the recovered enzyme component obtained by the 4th recovery was analyzed. The recovered enzyme (100 µL) was placed in a 1.5-mL centrifuge tube, and centrifuged at 15000 rpm for 5 minutes. Thereafter, the supernatant was removed to obtain a pellet at the bottom of the tube. The pellet was washed by addition of pure 100 µL, and a sample preparation buffer (EZ Apply, ATTO Corporation) was fed to the tube, followed by carrying out SDS-PAGE (e-PAGEL; gel concentration, 15%; ATTO Corporation). Staining was performed with Coomassie brilliant blue (BioSafecoomassie Stain, Bio-Rad Laboratories). For measuring the molecular weight, a molecular weight marker (PrecisionPlus Protein Standard, Kaleidoscope, Bio-Rad Laboratories) was used.

Figure 11:
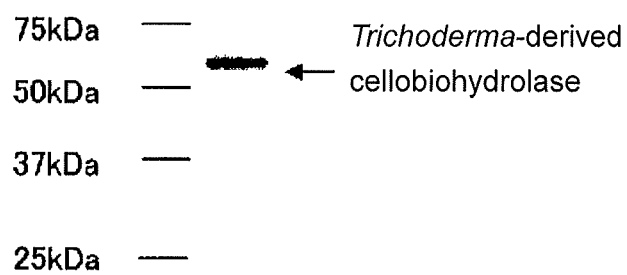
FIG. 11 is a diagram showing the result of SDS-PAGE of the water-insoluble *Trichoderma*-derived cellulase component.

The obtained result of the analysis by SDS-PAGE is shown in FIG. 11. Since the component had a molecular weight of about 50 to 60 kDa, it was revealed that Trichoderma-derived cellobiohydrolase was contained as a major component (FIG. 11).

Example 5

Effect of Water-Insoluble Trichoderma-Derived Cellulase Component as Recovered Enzyme Component The enzyme was recovered from the membrane fraction in Step 3 of Example 1 (pretreated cellulose 3) to obtain a recovered enzyme, which was then centrifuged at 15000 rpm for 5 minutes. Only the obtained supernatant was reused as the recovered enzyme, and the sugar yield observed as a result was compared with the results in Example 1. That is, Example 5 describes reuse of the recovered enzyme from which the water-insoluble Trichoderma-derived cellulase component was removed.

TABLE 6

| | | 0th hydrolysis | 1st hydrolysis | 2nd hydrolysis | 3rd hydrolysis | 4th hydrolysis | 5th hydrolysis | 6th hydrolysis |
|---|---|---|---|---|---|---|---|---|
| Pretreated cellulose 3 (Example 1) | Glc | 32 | 30 | 33 | 34 | 35 | 38 | 40 |
| | Xyl | 7 | 6 | 6 | 7 | 8 | 10 | 11 |
| Pretreated cellulose 3 | Glc | 32 | 32 | 32 | 31 | 31 | 30 | 30 |
| | Xyl | 7 | 6 | 6 | 7 | 6 | 6 | 6 |

That is, it was revealed that, in cases where the water-insoluble *Trichoderma*-derived cellulase component contained as a recovered enzyme is not removed, a higher sugar production rate can be obtained in the next reuse of the enzyme.

INDUSTRIAL APPLICABILITY

A sugar liquid can be efficiently produced from cellulose, and the obtained cellulose can be used as a sugar material for various fermentation products.

The invention claimed is:

1. A method of producing a sugar liquid by repeating a sugar liquid production process comprising (1) to (3):
   (1) adding a filamentous fungus-derived cellulase to cellulose which is a processed product obtained by subjecting a cellulose-containing biomass to alkaline treatment, hydrothermal treatment or dilute sulfuric acid treatment and has not been subjected to enzyme treatment to perform primary hydrolysis;
   (2) adding a fresh filamentous fungus-derived cellulase without adding cellulose to a hydrolysate formed in (1) without separating a solid residue in hydrolysate to perform secondary hydrolysis; and
   (3) subjecting another hydrolysate formed in (2) to solid-liquid separation to obtain a sugar liquid and recovering enzyme from the sugar liquid;
   wherein recovered enzyme obtained in (3) is used for (1) of next and later sugar liquid production processes, and as said filamentous fungus-derived cellulase in (1) of the sugar liquid production process, an enzyme component recovered from a cellulose hydrolysate produced by a filamentous fungus-derived cellulase is used.

2. The method according to claim 1, wherein said filamentous fungus-derived cellulase in (1) or (2) comprises a component derived from a culture liquid of a microorganism belonging to the genus *Trichoderma*.

3. The method according to claim 1, wherein said recovered enzyme comprises xylanase and/or xylosidase.

4. The method according to claim 1, wherein said recovered enzyme comprises a water-insoluble filamentous fungus-derived cellulase.

5. The method according to claim 1, wherein amounts of enzyme added in said primary hydrolysis and said secondary hydrolysis satisfy a following relation: an amount of said recovered enzyme added in (1) > an amount of said fresh enzyme added in (2).

6. The method according to claim 1, wherein recovery of said filamentous fungus-derived cellulase in (3) is carried out by filtering said sugar liquid through an ultrafiltration membrane and recovering said cellulase from the feed side.

7. The method according to claim 2, wherein said recovered enzyme comprises xylanase and/or xylosidase.

8. The method according to claim 2, wherein said recovered enzyme comprises a water-insoluble filamentous fungus-derived cellulase.

9. The method according to claim 3, wherein said recovered enzyme comprises a water-insoluble filamentous fungus-derived cellulase.

10. The method according to claim 1, wherein a reaction time of the primary hydrolysis in (1) is 15 minutes to 6 hours.

11. The method according to claim 10, wherein a reaction time of the secondary hydrolysis in (2) is 6 hours to 72 hours.

* * * * *